United States Patent
Tillander et al.

(10) Patent No.: US 10,271,890 B2
(45) Date of Patent: Apr. 30, 2019

(54) HIGH INTENSITY FOCUSED ULTRASOUND ENHANCED BY CAVITATION

(71) Applicant: KONINKLIJKE PHILIPS N.V., Eindhoven (NL)

(72) Inventors: Matti Oskari Tillander, Vantaa (FI); Max Oskar Kohler, Espoo (FI); Shunmugavelu Sokka, Belmont, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 997 days.

(21) Appl. No.: 14/241,552

(22) PCT Filed: Sep. 26, 2012

(86) PCT No.: PCT/IB2012/055123
§ 371 (c)(1),
(2) Date: Feb. 27, 2014

(87) PCT Pub. No.: WO2013/046131
PCT Pub. Date: Apr. 4, 2013

(65) Prior Publication Data
US 2015/0005756 A1 Jan. 1, 2015

Related U.S. Application Data

(60) Provisional application No. 61/539,648, filed on Sep. 27, 2011.

(51) Int. Cl.
*A61B 18/04* (2006.01)
*A61N 7/02* (2006.01)
(Continued)

(52) U.S. Cl.
CPC .......... *A61B 18/04* (2013.01); *A61B 17/2256* (2013.01); *A61N 7/02* (2013.01);
(Continued)

(58) Field of Classification Search
CPC .... A61N 2007/0004; A61N 2007/0021; A61N 2007/0039; A61N 2007/0043; A61N 7/02; A61N 7/022
See application file for complete search history.

(56) References Cited

U.S. PATENT DOCUMENTS

| 5,219,401 A | 6/1993 | Cathignol et al. |
| 6,508,774 B1 | 1/2003 | Acker et al. |
| (Continued) | | |

FOREIGN PATENT DOCUMENTS

| WO | 2003097162 A2 | 11/2003 |
| WO | 2009027920 A2 | 3/2009 |
| (Continued) | | |

*Primary Examiner* — Ronald Hupczey, Jr.
*Assistant Examiner* — Bo Ouyang

(57) ABSTRACT

A medical apparatus (600, 700, 800, 900) including a high intensity focused ultrasound system (602) generates focused ultrasonic energy (612) for sonicating within a target volume (620) of a subject (601). The high intensity focused ultrasound includes an ultrasonic transducer (606) with a controllable focus (618). The apparatus further includes a memory (634) containing machine executable for controlling the medical apparatus and a processor (628). The processor causes (100, 200, 300, 400, 502) ultrasonic cavitations at multiple cavitation locations (622, 1002) within the target volume using the high intensity focused ultrasound system, and sonicates (102, 206, 306, 402, 504) multiple sonication locations (1004) within the target volume using the high intensity focused ultrasound system. The multiple sonication locations and the multiple cavitation locations are targeted by adjusting the controllable focus.

15 Claims, 8 Drawing Sheets

(51) Int. Cl.
   *G01R 33/48*   (2006.01)
   *A61B 17/225*  (2006.01)
   *A61N 7/00*    (2006.01)
   *A61B 5/055*   (2006.01)
   *A61B 17/00*   (2006.01)
   *A61B 18/00*   (2006.01)
   *A61B 90/00*   (2016.01)

(52) U.S. Cl.
   CPC .......... *G01R 33/4804* (2013.01); *A61B 5/055* (2013.01); *A61B 2017/00084* (2013.01); *A61B 2018/00577* (2013.01); *A61B 2018/00648* (2013.01); *A61B 2018/00982* (2013.01); *A61B 2090/374* (2016.02); *A61N 2007/0065* (2013.01); *A61N 2007/0078* (2013.01); *A61N 2007/0091* (2013.01); *A61N 2007/0095* (2013.01); *F04C 2270/041* (2013.01); *G01R 33/4814* (2013.01)

(56) References Cited

U.S. PATENT DOCUMENTS

| | | |
|---|---|---|
| 7,771,359 B2 | 8/2010 | Dan |
| 2002/0082528 A1 | 6/2002 | Friedman et al. |
| 2003/0130599 A1 | 7/2003 | Restle et al. |
| 2007/0161902 A1 | 7/2007 | Dan |
| 2008/0058648 A1* | 3/2008 | Novak .............. A61B 17/22004 600/471 |
| 2009/0221902 A1 | 9/2009 | Myhr |
| 2009/0287083 A1* | 11/2009 | Kushculey ............... A61N 7/02 600/449 |
| 2010/0185080 A1 | 7/2010 | Myhr |
| 2010/0241036 A1* | 9/2010 | Vortman ................ A61B 8/467 601/3 |
| 2010/0280356 A1* | 11/2010 | Kohler .................... A61N 7/02 600/411 |
| 2010/0318002 A1 | 12/2010 | Prus et al. |
| 2011/0118600 A1* | 5/2011 | Gertner .................... A61B 8/06 600/439 |
| 2011/0251528 A1* | 10/2011 | Canney .................... A61N 7/02 601/3 |
| 2011/0257523 A1* | 10/2011 | Hastings ............... A61B 8/0891 600/439 |

FOREIGN PATENT DOCUMENTS

| | | |
|---|---|---|
| WO | 2010108104 A1 | 9/2010 |
| WO | 2011036475 A1 | 3/2011 |

* cited by examiner

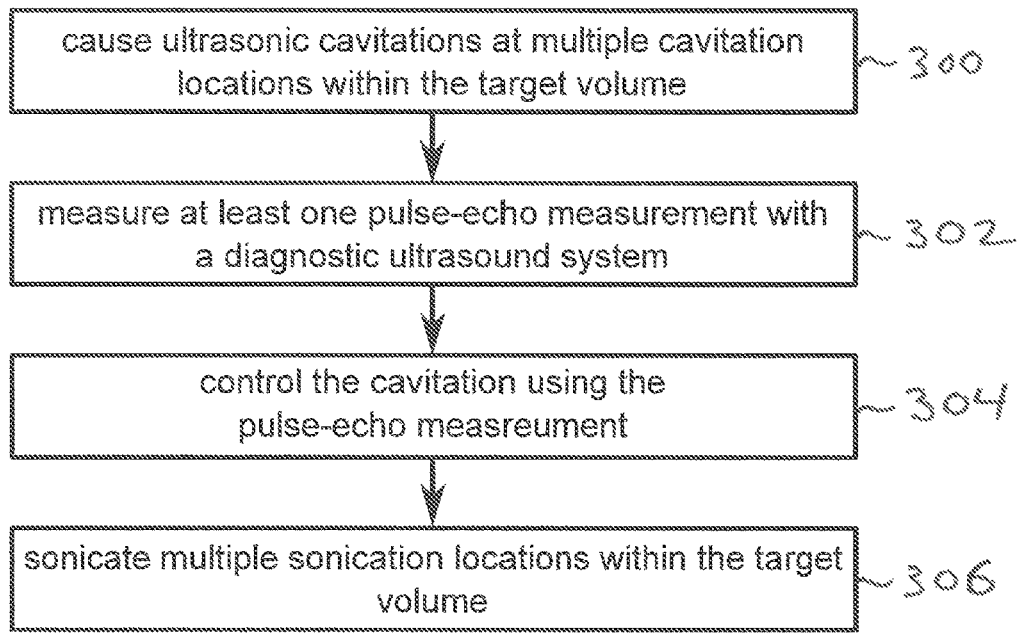
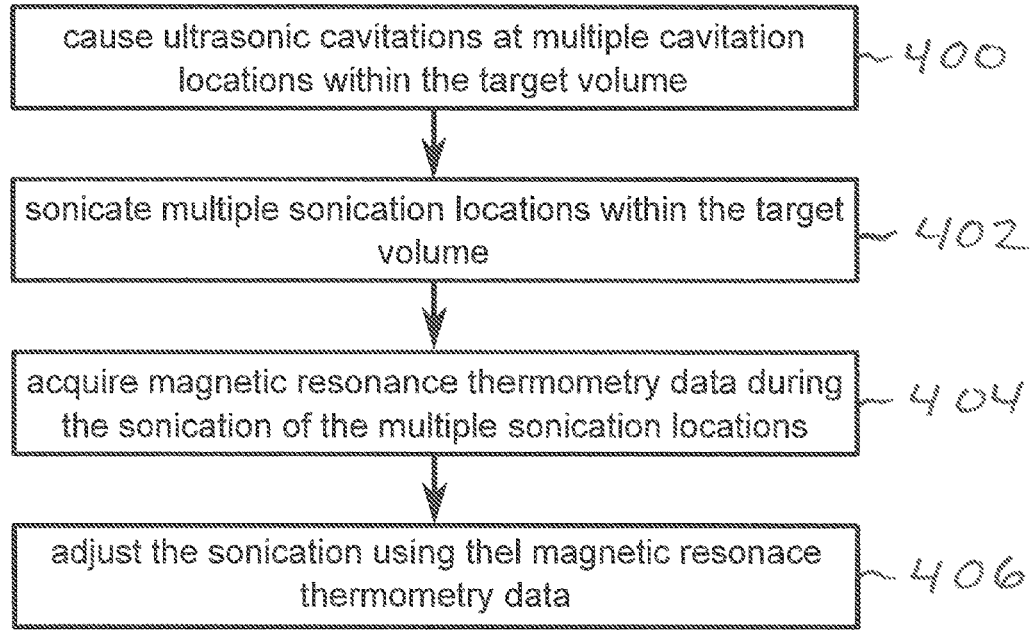

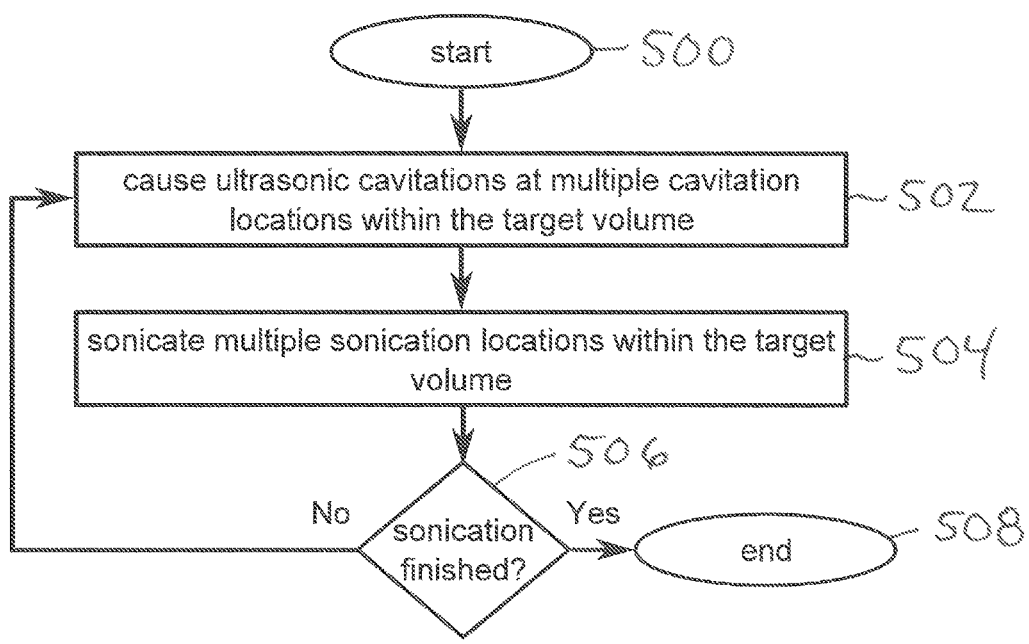

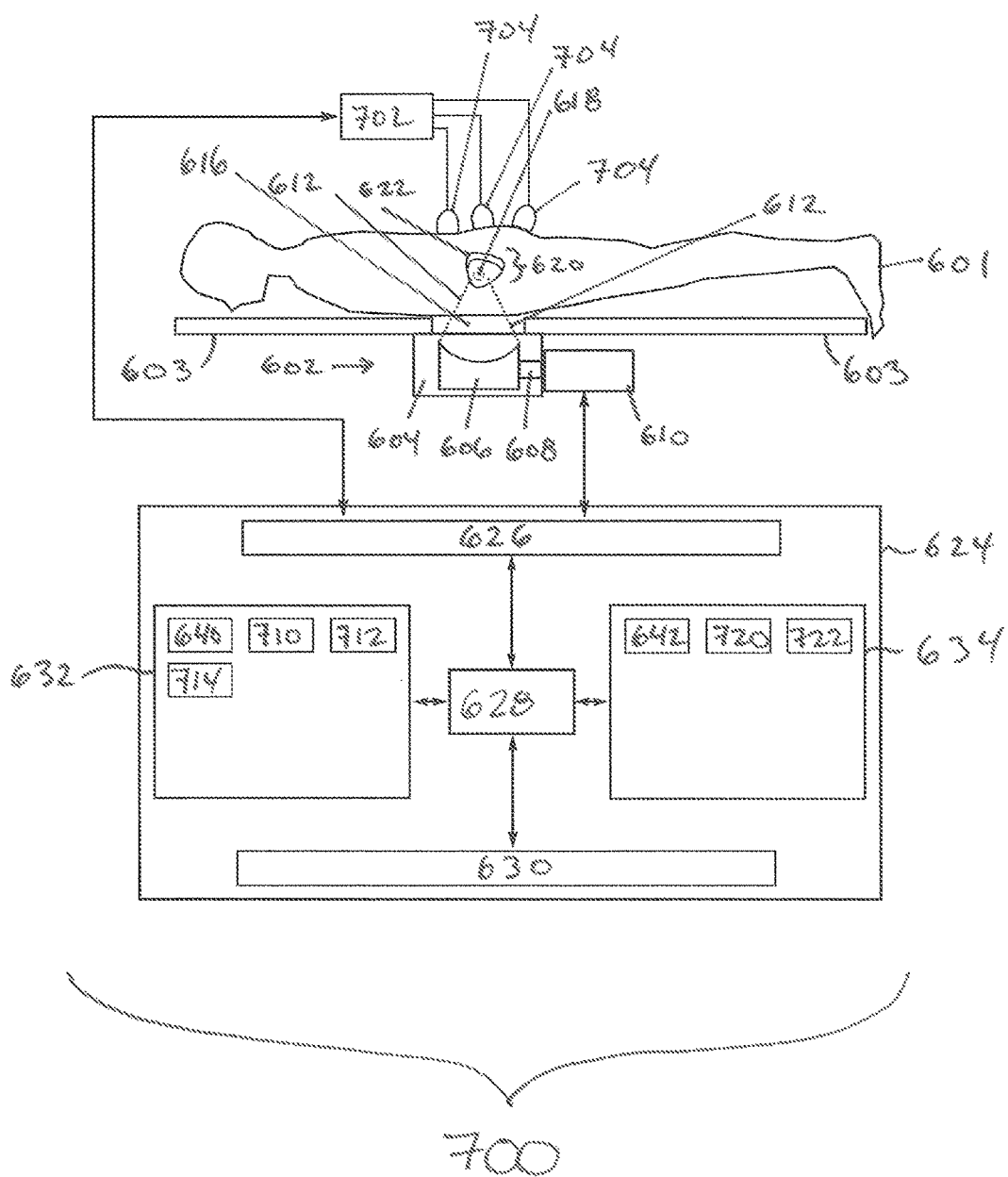

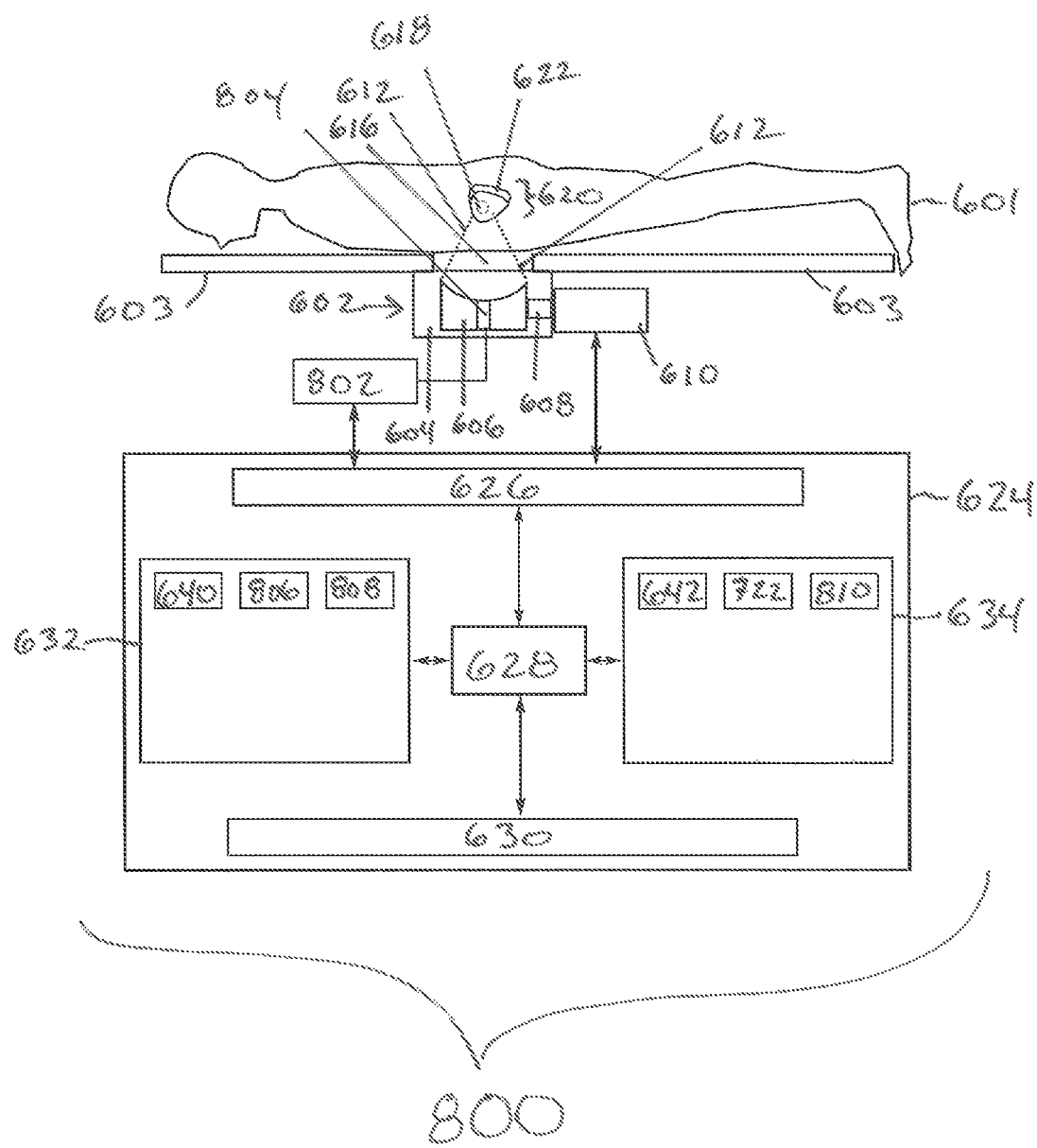

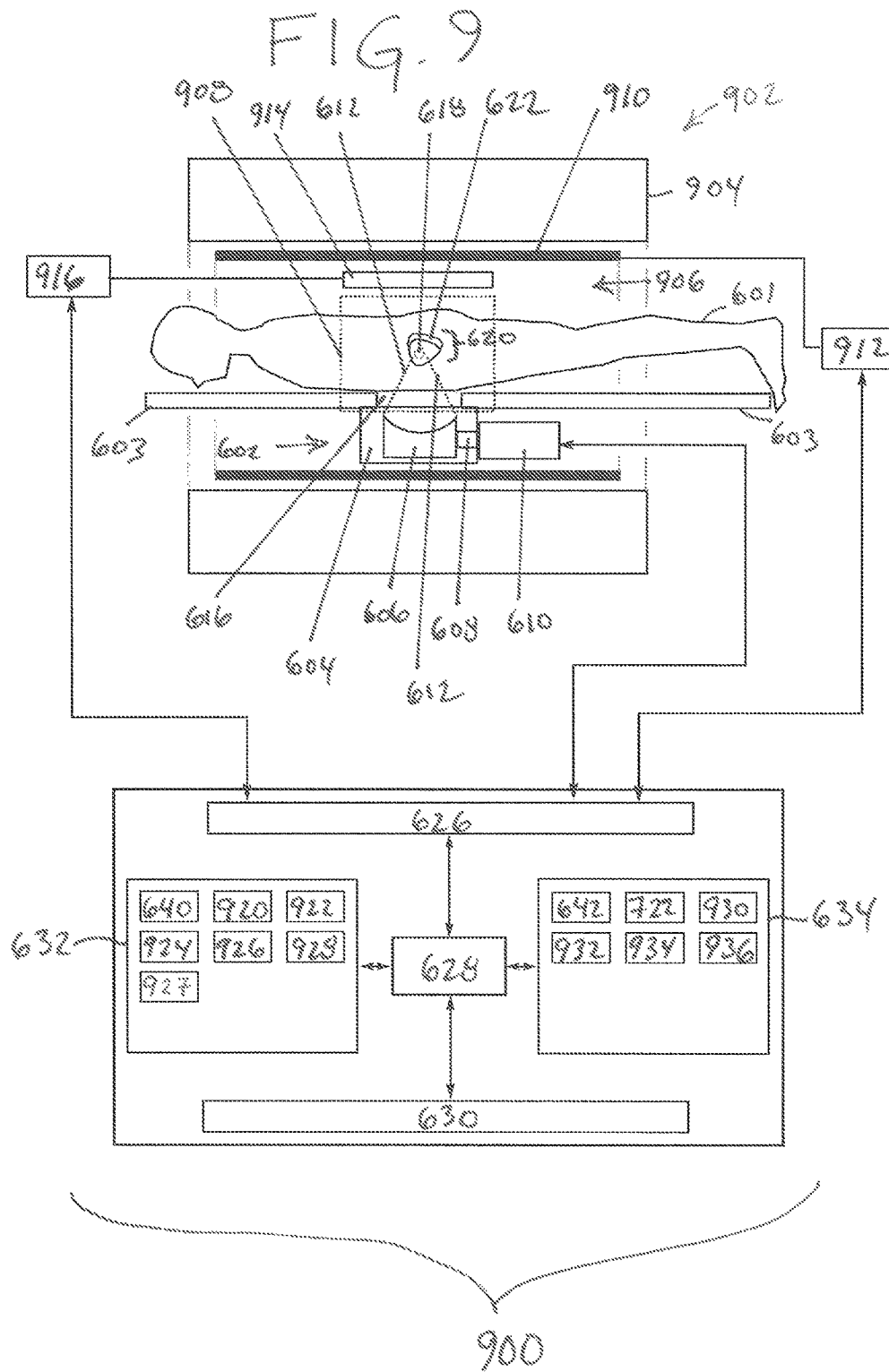

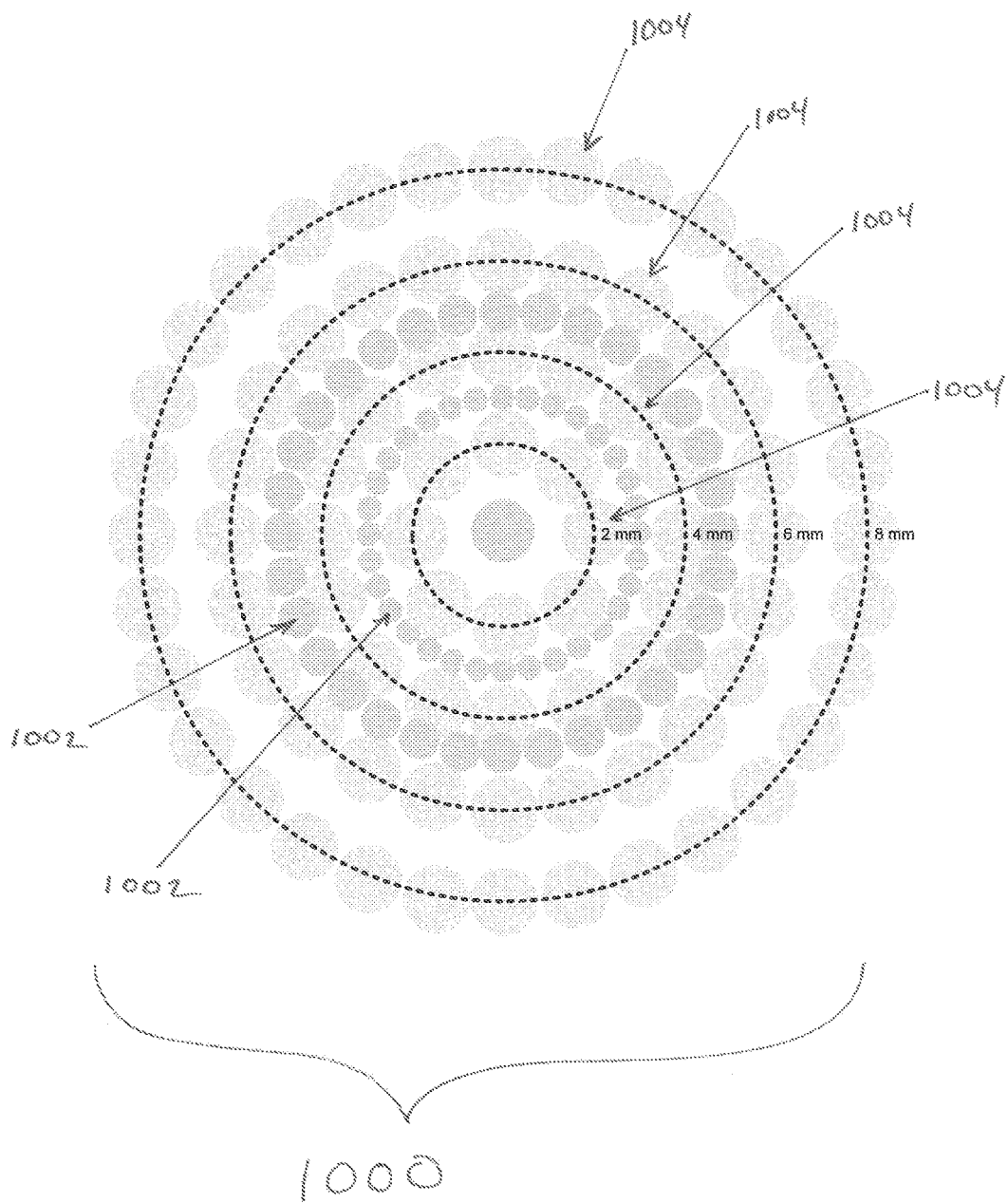

HIGH INTENSITY FOCUSED ULTRASOUND ENHANCED BY CAVITATION

CROSS-REFERENCE TO PRIOR APPLICATIONS

This application is the U.S. National Phase application under 35 U.S.C. § 371 of International Application No. PCT/IB2012/055123, filed on Sep. 26, 2012, which claims the benefit of U.S. Provisional Patent Application No. 61/539,648, filed on Sep. 27, 2011. These applications are hereby incorporated by reference herein.

TECHNICAL FIELD

The invention relates to high intensity focused ultrasound, in particular to cavitation enhanced sonication of a target volume.

BACKGROUND OF THE INVENTION

High-intensity focused ultrasound (HIFU) may be used to perform non-invasive thermal ablations. Conventional HIFU therapies rely on classical absorption of ultrasound energy through viscosity and heat conductivity losses that induce temperature increase in tissues. Usually the thermal ablations offer a good predictability both in temperature increase and ablated area. In volumetric HIFU therapy the focal point is steered electronically along concentric circles in the targeted area in order to achieve a controlled temperature increase on a larger area and hence, a larger ablated area.

If the target area is deep seated or for example well perfused, the applied energy needs to be increased either by increasing the acoustic intensity or the duration of the sonication. However, this increases also the thermal dose received by the intervening tissues and in some cases the heating of the skin might become critical and prevent the therapy.

When tissues are exposed to high-intensity ultrasound waves there is a risk of cavitation or other bubble activity. Usually the cavitation is tried to be avoided during HIFU therapy due to its unpredictable nature.

United States Patent Application Publication US 2010/0241036 discloses a system in which a first level of ultrasound is delivered to a target tissue resulting in the generation of micro-bubbles and delivers a second level of ultrasound energy to the target tissue region for a second duration.

International patent application publication WO 2003/097162 describes a focused ultrasound system which uses micro bubbles in a tissue region to enhance tissue coagulation.

SUMMARY OF THE INVENTION

The invention provides for a medical apparatus, a method of operating the medical apparatus, and a computer program product in the independent claims. Embodiments are given in the dependent claims.

In high-intensity focused ultrasound (HIFU) therapy tissues are exposed to ultrasonic waves that cause local temperature increase. With phased-array transducers the focal point can be moved electronically by manipulating the phases of the driving signals in order to enlarge the ablated area. This is called volumetric heating.

Usually in HIFU therapies the target is to cause ablations of tissues purely based on thermal mechanisms, but when intensities are high enough also other phenomena, such as cavitation, may appear. Cavitation or other bubble activity deteriorate the predictability of thermal ablations and is therefore to be minimized. However, bubbles may also increase the local heating and thus improve the therapy efficiency.

Cavitation enhanced heating in magnetic resonance imaging-guided HIFU (MR-HIFU) may use a short, high-intensity pulse prior to a longer sonication that has lower intensity. The purpose of the short pulse is to induce bubble activity in the targeted area. The induced bubbles oscillate nonlinearly in response to the ultrasound field generated by the following lower intensity sonication thus increasing the local absorption. Also, the combined interactions of bubbles with the short pulse and the longer sonication may generate an acoustic barrier in the focus that prevents acoustic propagation beyond the focus which also may cause increased local heating. Embodiments of the invention may create a bubble cloud or an acoustic barrier by causing ultrasonic cavitations at multiple locations within a target volume. Multiple sonication locations are sonicated, also known as a volumetric ablation, are performed after the bubble activity has been created.

The cavitation enhancement can be combined with volumetric ablations by using multiple cavitation inception pulses to different locations before volumetric sonications. The target is to create a wider bubble cloud or acoustic barrier for larger ablations. The creation of bubbles may be controlled by measuring the acoustic emission of bubble activity with passive cavitation detectors. The information gathered by the detectors may be also used in improving the following volumetric heating procedure.

Embodiments of the invention may increase the local absorption of ultrasound in HIFU therapy. This might be required for example in treatments of deep seated or well perfused tissues. The increased absorption results in shorter treatment times and/or reduced near field heating.

In some embodiments cavitation enhanced HIFU therapy is to combine it with volumetric heating. The short, very high-intensity cavitation inception pulse could now be applied to multiple locations in order to create a wider bubble cloud or acoustic barrier than what is achieved with one pulse. The following continuous wave sonication would be performed volumetrically.

Since utilization of acoustically created bubbles brings more uncertainty to the HIFU treatment, it may be beneficial to control the heating enhancement. The bubble activity may be measured using several methods. For example, acoustic emissions of cavitating bubbles can be detected with passive cavitation detectors, PCDs, which give information about the strength and the location of the bubble activity. Also, in the case of larger bubbles or gas pockets, simple pulse-echo measurements that show large reflections in impedance discontinuities may be used. If the therapy is performed under magnetic resonance imaging guidance, the quickly acquired thermal images can be used to measure the thermal behavior and work as a feedback in controlling the enhanced heating.

A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. References to a computer-readable storage medium should be interpreted as possibly being multiple computer-readable storage mediums. Various executable components of a program or programs may be stored in different locations. The computer-readable storage medium may for instance be multiple computer-readable storage medium within the same computer system. The computer-readable storage medium may also be computer-readable storage medium distributed amongst multiple computer systems or computing devices.

'Computer memory' or 'memory' is an example of a computer-readable storage medium. Computer memory is any memory which is directly accessible to a processor. Examples of computer memory include, but are not limited to: RAM memory, registers, and register files. References to 'computer memory' or 'memory' should be interpreted as possibly being multiple memories. The memory may for instance be multiple memories within the same computer system. The memory may also be multiple memories distributed amongst multiple computer systems or computing devices.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa. References to 'computer storage' or 'storage' should be interpreted as possibly being multiple storage devices. The storage may for instance be multiple storage devices within the same computer system or computing device. The storage may also be multiple storages distributed amongst multiple computer systems or computing devices.

A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses a interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

The Field Of View (FOV) is defined herein as meaning the volume for which an MRI image is constructed. The MRI data used to construct an MRI image is radio signals that are collected in the frequency domain. It is therefore important to note that the MRI data is converted into an image using a Fourier integral, and as a result tissues outside of the FOV contribute to the image.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

Magnetic resonance thermometry data is defined herein as being the recorded measurements of radio frequency signals emitted by atomic spins by the antenna of a Magnetic resonance apparatus during a magnetic resonance imaging scan which contains information which may be used for magnetic resonance thermometry. Magnetic resonance thermometry functions by measuring changes in temperature sensitive parameters. Examples of parameters that may be measured during magnetic resonance thermometry are: the proton resonance frequency shift, the diffusion coefficient, or changes in the T1 and/or T2 relaxation time may be used to measure the temperature using magnetic resonance. The proton resonance frequency shift is temperature dependent, because the magnetic field that individual protons, hydrogen atoms, experience depends upon the surrounding molecular structure. An increase in temperature decreases molecular screening due to the temperature affecting the hydrogen bonds. This leads to a temperature dependence of the proton resonant frequency.

The proton density depends linearly on the equilibrium magnetization. It is therefore possible to determine temperature changes using proton density weighted images.

The relaxation times T1, T2, and T2-star (sometimes written as T2*) are also temperature dependent. The reconstruction of T1, T2, and T2-star weighted images can therefore be used to construct thermal or temperature maps.

The temperature also affects the Brownian motion of molecules in an aqueous solution. Therefore pulse sequences which are able to measure diffusion coefficients such as a pulsed diffusion gradient spin echo may be used to measure temperature.

One of the most useful methods of measuring temperature using magnetic resonance is by measuring the proton resonance frequency (PRF) shift of water protons. The resonant frequency of the protons is temperature dependent. As the temperature changes in a voxel the frequency shift will cause the measured phase of the water protons to change. The temperature change between two phase images can therefore be determined. This method of determining temperature has the advantage that it is relatively fast in comparison to the other methods. The PRF method is discussed in greater detail than other methods herein. However, the methods and techniques discussed herein are also applicable to the other methods of performing thermometry with magnetic resonance imaging.

An 'ultrasound window' as used herein encompasses a window which is able to transmit ultrasonic waves or energy. Typically a thin film or membrane is used as an ultrasound window. The ultrasound window may for example be made of a thin membrane of BoPET (Biaxially-oriented polyethylene terephthalate).

In one aspect the invention provides for a medical apparatus comprising a high-intensity focused ultrasound system configured for generating focused ultrasonic energy for sonicating within a target volume of a subject. The high-intensity focused ultrasound comprises an ultrasonic transducer with a controllable focus. The medical apparatus further comprises a memory containing machine executable instructions for controlling the medical apparatus. The medical apparatus further comprises a processor for controlling the medical apparatus. The processor executes the machine executable instructions. Execution of the instructions cause the processor to cause ultrasonic cavitations at multiple cavitation locations within the target volume using the high-intensity focused ultrasound system. The multiple cavitation locations are targeted by adjusting the controllable focus.

As used herein sonication is the heating of tissue using ultrasound. As used herein cavitation is the formation of empty cavities or bubbles in a liquid by using ultrasound and the immediate implosion of them also by using ultrasound. References in the claims to sonicating a target using ultrasound may be interpreted as the heating of the target using ultrasound with an intensity below a threshold which induces cavitation. References in the claims to causing cavitation in a target using ultrasound may be interpreted as a sonication performed with sufficient ultrasound intensity to induce the formation of bubbles and subsequent cavitation of them.

Execution of the instructions further causes the processor to sonicate multiple sonication locations within the target volume using the high-intensity focused ultrasound system. The multiple sonication locations are targeted by adjusting the controllable focus. The controllable focus of the ultrasonic transducer may be an electronically controllable focus. For instance the ultrasonic transducer may comprise multiple transducer elements. By controlling the amplitude and in particular the phase to each of the elements the constructive and destructive interference of the ultrasound generated by each of the elements enables the focus to be controlled or adjusted. This embodiment may be beneficial because regions which have been cavitated using ultrasound transmit a much smaller amount of ultrasound. In this embodiment the first ultrasonic cavitation is caused in the target volume. Next the target volume is sonicated. By first performing the ultrasonic cavitations a greater portion of the ultrasound energy remains within the target volume.

In another embodiment the medical apparatus further comprises a passive cavitation detector. A passive cavitation detector as used herein is a transducer or sensor used to detect ultrasonic emissions brought about by the applied ultrasound sonications. It is possible to separate the ultrasonic emissions caused by the cavitating bubbles from other emissions for example by examining the frequency content of the emissions. Cavitation activity is often seen as emissions at frequency that is half of the frequency that the ultrasound is generated at or as increased broad band noise. Frequency content gives information on both the magnitude and type of bubble activity. Execution of the instructions causes the processor to measure a cavitation spectrum using the passive cavitation detector during the causing of the ultrasonic cavitation. A cavitation spectrum as used herein encompasses ultrasonic measurements of cavitation in the frequency domain.

The cavitation spectrum can be used in several ways to determine the magnitude or quantity of cavitation that is occurring: The magnitude of the peaks in the frequency domain of the cavitation spectrum may correlates well with the population of bubbles undergoing cavitation. The spread of activity in the frequency domain may also be used. In general, if there is increased broadband emission in the cavitation spectrum, then there is also a greater magnitude of cavitation activity. This may increase the level of white noise is a very good approximation of cavitation magnitude. Therefore, the cavitation energy as would be calculated from the integral of the frequency spectrum may be an indicator of changes in cavitation magnitude.

Execution of the instructions further causes the processor to control at least partially the cavitation in accordance with the cavitation spectrum by controlling the high-intensity focused ultrasound system. This embodiment may be beneficial because the processor is able to determine with the passive cavitation detector the success of inducing cavitation. If the cavitation signal is too low then more energy can be provided to the ultrasonic transducer. Execution of the instructions further causes the processor to control at least partially the cavitation in accordance with the cavitation spectrum by controlling the high-intensity focused ultrasound system. Using the cavitation spectrum measured by the cavitation detector the magnitude or degree of cavitation can be detected. This may be beneficial because the transmission of ultrasound through different types or regions of tissue may not always be uniform. Measuring the cavitation spectrum enables the generation of consistent cavitation every time.

In another embodiment the medical apparatus further comprises multiple passive cavitation detectors. Execution of the instructions further causes the processor to detect a cavitation location using the multiple cavitation detectors during the causing of the ultrasonic cavitation. Execution of the instructions further causes the processor to detect a cavitation location using the multiple cavitation detectors during the causing of the ultrasonic cavitation. The multiple passive cavitation detectors can each detect ultrasound generated by cavitation. Data from the multiple detectors or acoustic sensors can be used to triangulate the location within the subject. Execution of the instructions further causes the processor to control at least partially the cavitation in accordance with the cavitation location by controlling the high-intensity focused ultrasound system. One or more of the multiple cavitation detectors may also be used to detect the cavitation spectrum.

In another embodiment the apparatus further comprises an ultrasound measurement transducer configured for performing pulse-echo measurements. The ultrasound measurement transducer may for instance be a diagnostic ultrasound system. The diagnostic ultrasound system may be integrated into the high-intensity focused ultrasound system which may for instance incorporate an ultrasound measurement transducer into the ultrasonic transducer of the high-intensity focused ultrasound system. In other embodiments the ultrasound measurement transducer is a separate transducer independent of the high-intensity focused ultrasound system's ultrasonic transducer. Execution of the instructions further causes the processor to measure at least one pulse-echo measurement with the ultrasound measurement transducer during or after the causing of the ultrasonic cavitation.

Execution of the instructions further causes the processor to control at least partially the cavitation in accordance with the pulse-echo measurement by controlling the high-intensity focused ultrasound system. A large amount of small bubbles within the subject caused by the cavitation is efficient at blocking ultrasound. For this reason performing pulse-echo measurements where a pulse is sent out by the transducer and an echo is recorded the diagnostic or ultrasound measurement transducer is very efficient at detecting the bubbles from the cavitation. The pulse-echo measurements can for instance be used for determining the location of bubbles caused by the cavitation. In this respect the location of the bubbles can be used to control the high-intensity focused ultrasound system to more accurately target formation of bubbles by a cavitation.

In another embodiment the medical apparatus further comprises a magnetic resonance imaging system for acquiring magnetic resonance thermometry data from an imaging zone. The target volume is within the imaging zone. Execution of the instructions further causes the processor to acquire the magnetic resonance thermometry data during the sonication of the multiple sonication locations. Execution of the instructions further causes the processor to adjust the sonication of the multiple sonication locations in accordance with the magnetic resonance thermometry data. This embodiment may be advantageous because the acquisition of magnetic resonance thermometry data allows the direct determination or spatially dependent temperature within the subject. This may be used to monitor how efficiently the ultrasonic transducer is heating a volume of the subject. A knowledge of this heating can then be used in a feedback loop to adjust the control of the sonication process. This embodiment may be beneficial because it may enable more efficient sonications of the subject resulting in reduced treatment time or a greater throughput for the medical apparatus.

In another embodiment the magnetic resonance imaging system is further configured for acquiring phase image magnetic resonance data. Phase image magnetic resonance data as used herein is magnetic resonance data which contains information detailing the phase of shift during magnetic resonance data acquisition. Execution of the instructions further causes the processor to acquire the phase image magnetic resonance data during the causing of ultrasonic cavitations at multiple cavitation locations. Execution of the instructions further causes the processor to adjust the causing of the ultrasonic cavitations in accordance with the phase image magnetic resonance data. This embodiment may be beneficial because the phase image magnetic resonance data may be useful for locating the volume and density of bubbles produced by cavitation. Having a direct measurement of the location and the magnitude of bubbles it may be useful for using in a control loop where phase image data is acquired and then used for correcting the sonication of the patient.

In another embodiment the causing of the ultrasonic cavitations and the sonication of multiple sonication locations is repeated by the processor multiple times. Essentially the production of ultrasonic cavitations and the sonication of multiple locations may be done repeatedly in a loop. This may be beneficial because after cavitation occurs the bubbles will disappear or disperse after a period of time.

In another embodiment the multiple cavitation locations lie on a surface. The surface may for instance be a flat surface or it may be a curved surface such as a manifold. This embodiment may be beneficial because the bubbles caused by cavitation are efficient at absorbing ultrasound which results in a attenuation of the ultrasound. For instance a surface of the target zone that is furthest away from the ultrasound transducer may have multiple cavitation locations sonicated. This would then effectively block ultrasound from leaving the target zone. This may have the benefit of reducing heating in regions beyond the target zone and it may also help to increase the amount of heating within the target zone.

In another embodiment the multiple cavitation locations are arranged in a circular pattern. This embodiment may be beneficial because the multiple cavitation locations may form a shield or a block which reduces the amount of ultrasound which goes through it.

In another embodiment the multiple cavitation locations are identical with the multiple sonication locations. This embodiment may be particularly beneficial because this will help to increase the efficiency of sonication at the multiple cavitation locations.

In another embodiment ultrasonic cavitations at multiple cavitation locations form an acoustic barrier. The bubbles generated by the ultrasonic cavitations make it difficult for ultrasound to pass the region with the bubbles. In this way forming cavitations at the multiple cavitation locations may form an acoustic barrier which blocks or partially blocks ultrasound from traveling through it.

In another aspect the invention provides for a method of operating a medical apparatus. The medical apparatus comprises a high-intensity focused ultrasound system configured for generating focused ultrasonic energy for sonicating within a target volume of a subject. The high-intensity focused ultrasound system comprises an ultrasonic transducer with a controllable focus. The method comprises the step of causing ultrasonic cavitations at multiple cavitation locations within the target volume using the high-intensity focused ultrasound system. The multiple cavitation locations are targeted by adjusting the controllable focus. The method further comprises the step of sonicating multiple cavitation locations within the target volume using the high-intensity focused ultrasound system. The multiple sonication locations are targeted by adjusting the controllable focus. The advantages of this embodiment have been previously given.

In another embodiment the medical apparatus further comprises a passive cavitation detector. The method further comprises the step of detecting a cavitation spectrum using the passive cavitation detector during the causing of the ultrasonic cavitation. The method further comprises the step of controlling at least partially the cavitation in accordance with the cavitation spectrum by controlling the high-intensity focused ultrasound system. The advantages of this embodiment have been previously discussed.

In another embodiment the medical apparatus further comprises multiple passive cavitation detectors. The method further comprises the step of detecting a cavitation location using the multiple cavitation detectors during the causing of the ultrasonic cavitation. The method further comprises the step of controlling at least partially the cavitation in accordance with the cavitation location by controlling the high-intensity focused ultrasound system. Advantages of this embodiment have been previously discussed.

In another aspect the invention provides for a computer program product comprising machine executable instructions for execution by a processor controlling a medical apparatus. The medical apparatus comprises a high-intensity focused ultrasound system configured for generating focused ultrasonic energy for sonicating within a target volume of a subject. The high-intensity focused ultrasound comprises an ultrasonic transducer with a controllable focus. Execution of the instructions causes the processor to cause ultrasonic cavitations at multiple cavitation locations within the target volume using the high-intensity focused ultrasound system. The multiple cavitation locations are targeted by adjusting the controllable focus. Execution of the instructions further causes the processor to sonicate multiple sonication locations within the target volume using the high-intensity focused ultrasound system. The multiple sonication locations are targeted by adjusting the controllable focus. Advantages of this embodiment have been previously discussed.

BRIEF DESCRIPTION OF THE DRAWINGS

In the following preferred embodiments of the invention will be described, by way of example only, and with reference to the drawings in which:

FIG. 3 shows a flow diagram which illustrates a method according to a further embodiment of the invention;

FIG. 4 shows a flow diagram which illustrates a method according to a further embodiment of the invention;

FIG. 5 shows a flow diagram which illustrates a method according to a further embodiment of the invention;

FIG. 7 illustrates a medical apparatus according to a further embodiment of the invention;

FIG. 8 illustrates a medical apparatus according to a further embodiment of the invention;

FIG. 9 illustrates a medical apparatus according to a further embodiment of the invention; and FIG. 10 shows a pattern of cavitation and sonication locations 1000.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
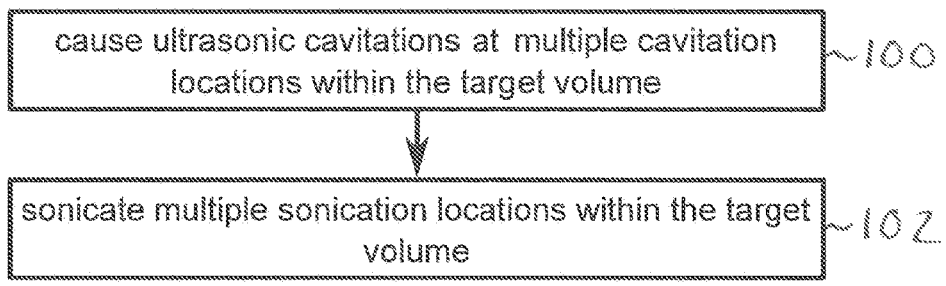
FIG. 1 shows a flow diagram which illustrates a method according to an embodiment of the invention.

FIG. 1 shows a flow diagram which illustrates a method according to an embodiment of the invention. First in step 100 ultrasonic cavitations at multiple cavitation locations are caused within a target volume using a high-intensity focused ultrasound system. Next in step 102 multiple sonication locations are sonicated within the target volume.

Figure 2:
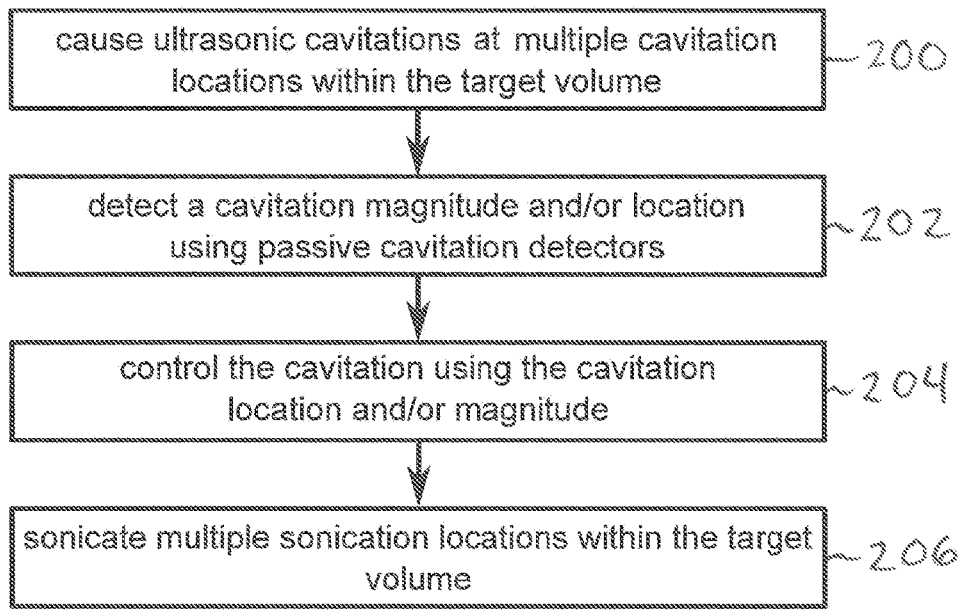
FIG. 2 shows a flow diagram which illustrates a method according to a further embodiment of the invention.

FIG. 2 shows a flow diagram which illustrates a method according to a further embodiment of the invention. First in step 200 ultrasonic cavitations are caused at multiple cavitation locations within the target volume. Next at step 202 a cavitation spectrum and/or cavitation location are detected using passive cavitation detector or detectors. Detecting the magnitude will give information about the strength or magnitude of the cavitation and of course the cavitation location is useful in determining the location of the cavitation. Next in step 204 the cavitation is controlled using the cavitation location and/or magnitude. The positioning of the high-intensity focused ultrasound system can be adjusted to put the cavitation in the proper location or the amount of power supplied to the ultrasonic transducer can be adjusted so that the cavitation is of the proper magnitude. Finally in step 206 multiple sonication locations are sonicated within the target volume.

FIG. 3 shows a flow diagram which illustrates a method according to a further embodiment of the invention. In step 300 ultrasonic cavitations are caused at multiple cavitation locations within the target volume using a high-intensity focused ultrasound system. Next in step 302 at least one pulse-echo measurement is measured with a diagnostic ultrasound system. This is performed either during or after some of the multiple cavitation locations have been cavitated. In step 304 the cavitation is controlled using the pulse-echo measurements. The pulse-echo measurements are useful for determining the location of the cavitations. In this way the location of where a cavitation has been generated may be directly measured and then adjusted. The position of the cavitation can be adjusted using the adjustable focus of the ultrasound transducer. Next in step 306 multiple sonication locations are sonicated within the target volume.

FIG. 4 shows a flow diagram which illustrates a method according to a further embodiment of the invention. First in step 400 ultrasonic cavitations are caused at multiple cavitation locations within the target volume using a high-intensity focused ultrasound system. Next in step 402 multiple sonication locations are sonicated within the target volume. The sonications are used to heat regions within the target volume. In step 404 magnetic resonance thermometry data is acquired during the sonication of the multiple sonication locations. The acquiring of the magnetic resonance thermometry data allows a direct measurement of the heating that has been performed during the sonication. Next in step 406 the sonication is adjusted using the magnetic resonance thermometry data. For instance a thermal map, a temperature change map, or increase map of the deposited energy may be constructed using the magnetic resonance thermometry data. This may then be used to adjust the sonication to more efficiently or uniformly heat the target volume.

FIG. 5 shows a flow diagram which illustrates a method according to a further embodiment of the invention. In step 500 the method starts. Next in step 502 ultrasonic cavitations are caused at multiple cavitation locations within the target volume using a high-intensity focused ultrasound system. Next in step 504 multiple sonication locations are sonicated within the target volume. In some instances a sonication may need to last longer than the bubbles which were caused by the cavitation. In this case the decision box 506 determines if the sonication is finished or not. If the sonication is not finished then step 502 may be repeated to generate more bubbles by causing more ultrasonic cavitations at multiple cavitation locations within the target volume. If the sonication is finished then the method ends in step 508. It should be noted that any of the methods presented in FIGS. 1-5 may have various elements combined to create new methods.

Figure 6:
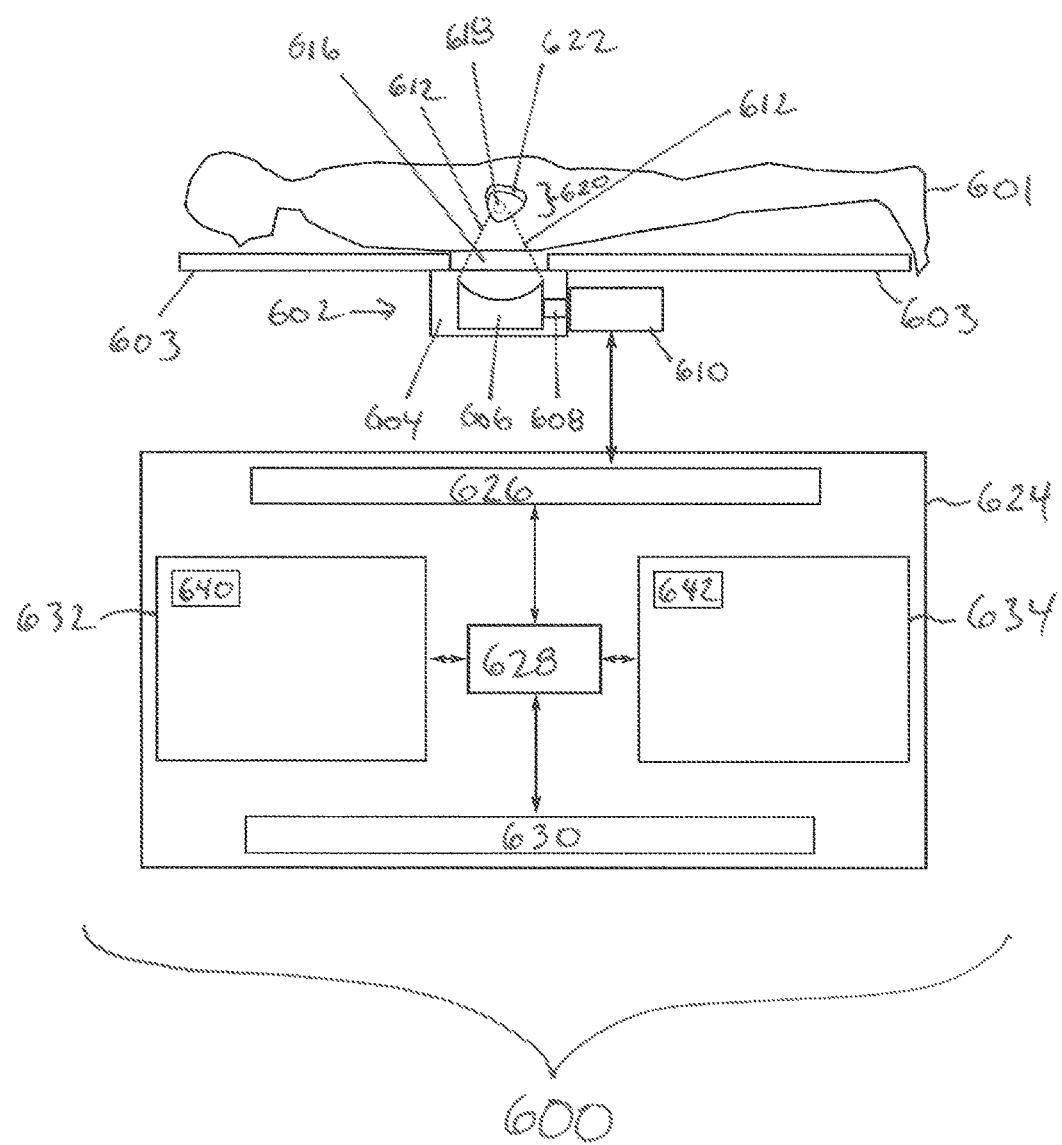
FIG. 6 illustrates a medical apparatus according to an embodiment of the invention.

FIG. 6 illustrates a medical apparatus 600 according to an embodiment of the invention. The embodiment shown in FIG. 6 comprises a temperature treatment system which is a high-intensity focused ultrasound system 602 for sonicating a subject 601. The high-intensity focused ultrasound system is mounted below a subject support 603. The subject 601 is resting on the subject support 603. The high-intensity focused ultrasound system comprises a fluid-filled chamber 604. Within the fluid-filled chamber 604 is an ultrasound transducer 606. Although it is not shown in this figure the ultrasound transducer 606 may comprise multiple ultrasound transducer elements each capable of generating an individual beam of ultrasound. This may be used to steer the location of a sonication point 618 electronically by controlling the phase and/or amplitude of alternating electrical current supplied to each of the ultrasound transducer elements.

The ultrasound transducer 606 is connected to a mechanism 608 which allows the ultrasound transducer 306 to be repositioned mechanically. The mechanism 608 is connected to a mechanical actuator 310 which is adapted for actuating the mechanism 608. The mechanical actuator 610 also represents a power supply for supplying electrical power to the ultrasound transducer 606. In some embodiments the power supply may control the phase and/or amplitude of electrical power to individual ultrasound transducer elements. In some embodiments the mechanical actuator/power supply 610 is located outside of the bore 604 of the magnet 602

The ultrasound transducer 606 generates ultrasound which is shown as following the path 612. The ultrasound 612 goes through the fluid-filled chamber 608 and through an ultrasound window 614. In this embodiment the ultrasound then passes through a gel pad 616. The gel pad is not necessarily present in all embodiments but in this embodiment there is a recess in the subject support 603 for receiving a gel pad 616. The gel pad 616 helps couple ultrasonic power between the transducer 606 and the subject 601. After passing through the gel pad 616 the ultrasound 612 passes through the subject 601 and is focused to a sonication point 618. The sonication point is understood to be a finite volume or localized volume to which the ultrasound is focused. The sonication point 618 is being focused within a target volume 620. The sonication point 618 may be moved through a combination of mechanically positioning the ultrasonic transducer 606 and electronically steering the position of the sonication point 618.

A portion of the target volume 620 is labeled 622. The region labeled 622 shows a region where there are multiple cavitation locations. The multiple cavitation locations in this example 622 are on a far surface of the target volume 620 from the ultrasonic transducer 606. The bubbles caused by cavitation at the multiple cavitation locations 622 greatly attenuate the ultrasound 612. Effectively the multiple cavitation locations 622 form a shield or barrier which obstructs or greatly attenuates the ultrasound 612. This confines the ultrasound 612 to the remainder of the target volume 620.

The high intensity focused ultrasound system 602 is shown as being connected to a hardware interface 626 of the computer 624. The hardware interface 626 is connected to a processor 628. The hardware interface 626 enables the processor 628 to send and receive data and commands to control the operation and function of the medical apparatus 600. The processor 328 is further connected to a user interface 630, computer storage 632 and computer memory 634.

The computer storage 632 is shown as containing a treatment plan 640. The treatment plan may contain detailed instructions for the high-intensity focused ultrasound system 602 for performing cavitations of the multiple cavitation locations 622 and for sonication of the target volume 620.

The computer memory 634 is shown as containing control module 642. The control module 642 contains machine executable instructions which allow the processor 628 to control the operation and function of the medical apparatus 600. For instance the control module 642 may use the treatment plan 640 to generate control sequences for controlling the operation and function of the high-intensity focused ultrasound system 602.

FIG. 7 shows a diagram which illustrates a medical apparatus 700 according to a further embodiment of the invention. The embodiment shown in FIG. 7 is similar to that shown in FIG. 6. The embodiment shown in FIG. 7 in addition has a passive cavitation detector 702. The passive cavitation detector 702 comprises several acoustic sensors 704 distributed on the surface of the subject 601. The acoustic sensors 704 are able to detect the ultrasound generated by bubbles cavitating at the multiple cavitation locations 622. From this ultrasound the passive cavitation detector 702 is able to record cavitation detector data 710. The passive cavitation detector 702 is connected to the computer 624 via the hardware interface 626. The computer storage 632 is shown as containing cavitation detector data 710 that was acquired using the passive cavitation detector 702. The computer storage 632 is further shown as containing a cavitation spectrum 712 and cavitation locations 714 both which were calculated from the cavitation detector data 710. Data from multiple acoustic sensors 704 can be used to triangulate the location of cavitating bubbles.

The computer memory 634 is further shown as containing a cavitation data calculation module 720. The cavitation data calculation module 720 contains computer executable code which enables the processor 628 to calculate cavitation spectrums 612 and/or cavitation locations 714 from cavitation detector data 710. The computer memory 634 is further shown as containing a cavitation adjustment control module. The cavitation adjustment control module contains computer executable code which enables the processor 628 to generate commands for adjusting and controlling the high-intensity focused ultrasound system 602 in order to adjust the cavitation of the multiple cavitation locations 622. The cavitation adjustment control module 622 uses either the cavitation detector data 710 or the cavitation spectrum 712 and cavitation locations 714 as input. The cavitation detector 710 would most likely be acquired continuously during the cavitation of the multiple cavitation locations 622. The acquisition of the cavitation detector 710 and the control of the high-intensity focused ultrasound system 602 by the cavitation adjustment control module 722 would therefore form a closed control loop.

FIG. 8 shows a medical apparatus 800 according to a further embodiment of the invention. The embodiment shown in FIG. 8 is similar to the embodiment shown in FIG. 8. In FIG. 8 a diagnostic ultrasound system 802 has been added to the medical apparatus 800. A diagnostic ultrasound transducer 804 is incorporated into the ultrasound transducer 606. In some alternative embodiments the diagnostic ultrasound transmission 804 is separate from the ultrasound transducer 606. The diagnostic ultrasound transducer 804 is connected to the diagnostic ultrasound system 802. The diagnostic ultrasound system 802 is also connected to the hardware interface 626. The control module 643 in this embodiment is also adapted for controlling the diagnostic ultrasound system 802.

The computer storage 632 is shown as further containing diagnostic ultrasound data 806. The diagnostic ultrasound data 806 in this embodiment is equivalent to pulse-echo measurements. The computer storage 632 is further shown as containing a diagnostic ultrasound image 808. The diagnostic ultrasound image 808 was reconstructed from the diagnostic ultrasound data 806. The computer memory 634 is further shown as containing an image reconstruction module 810. The image reconstruction module 810 contains computer executable code for reconstructing the diagnostic ultrasound image 808 from the diagnostic ultrasound data 806. The computer memory 634 is further shown as containing image segmentation module 812. The image segmentation module 812 contains computer executable code for identifying the location of the moving target 620 within the diagnostic ultrasound image 808. The computer memory is further shown as containing a cavitation adjustment control module 722. In this embodiment the cavitation adjustment control module uses the diagnostic ultrasound data 806 and/or the diagnostic ultrasound image 808 as input for the control loop.

FIG. 9 shows a therapeutic apparatus 900 according to a further embodiment of the invention. The therapeutic apparatus 900 shown in FIG. 9 is similar to the therapeutic apparatus 600 shown in FIG. 6. The therapeutic apparatus 900 comprises a magnetic resonance imaging system 902. The magnetic resonance imaging system comprises a magnet 904. The magnet 904 is a cylindrical type superconducting magnet with a bore 906 through the center of it. The high intensity focused ultrasound system 602 is located within the bore 906.

The magnet 904 has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 906 of the cylindrical magnet there is an imaging zone 408 where the magnetic field is strong and uniform enough to perform magnetic resonance imaging.

Within the bore 906 of the magnet there is also a set of magnetic field gradient coils 910 which are used for acquisition of magnetic resonance data to spatially encode magnetic spins within the imaging zone 908 of the magnet 904. The magnetic field gradient coils are connected to a magnetic field gradient coil power supply 912. The magnetic field gradient coils 910 are intended to be representative. Typically magnetic field gradient coils contain three separate sets of coils for spatially encoding in three orthogonal spatial directions. A magnetic field gradient power supply 912 supplies current to the magnetic field gradient coils 910. The current supplied to the magnetic field coils is controlled as a function of time and may be ramped or pulsed.

Adjacent to the imaging zone 908 is a radio-frequency coil 914 for manipulating the orientations of magnetic spins within the imaging zone 908 and for receiving radio transmissions from spins also within the imaging zone. The radio-frequency coil may contain multiple coil elements. The radio-frequency coil may also be referred to as a channel or an antenna. The radio-frequency coil 914 is connected to a radio frequency transceiver 916. The radio-frequency coil 914 and radio frequency transceiver 916 may be replaced by separate transmit and receive coils and a separate transmitter and receiver. It is understood that the radio-frequency coil 914 and the radio-frequency transceiver 916 are representative. The radio-frequency coil 914 is intended to also represent a dedicated transmit antenna and a dedicated receive antenna. Likewise the transceiver 916 may also represent a separate transmitter and receivers.

The computer storage 632 is shown as additionally containing a pulse sequence 920. A pulse sequence as used herein encompasses a set of instructions which enables the processor 928 to control the magnetic resonance imaging system 902 to acquire the magnetic resonance data 924. The computer storage 332 is further shown as containing magnetic resonance data 924 that was acquired using the magnetic resonance imaging system 902. The computer storage 332 is further shown as containing a magnetic resonance thermometry pulse sequence 922. The magnetic resonance thermometry pulse sequence 922 is a pulse sequence which enables the magnetic resonance imaging system 902 to acquire magnetic resonance thermometry data 927. The computer storage is further shown as containing magnetic resonance thermometry data 927 acquired using the magnetic resonance imaging system 902. The computer storage 632 is further shown as containing a magnetic resonance image 926 that has been reconstructed from the magnetic resonance data 924. The computer storage 332 is further shown as containing a temperature map 928 that has been reconstructed from the magnetic resonance thermometry data 927. In this some cases the magnetic resonance data 924 may comprises the magnetic resonance thermometry data 927. The computer memory 334 is further shown as containing an image reconstruction module 930 which was used for reconstructing the magnetic resonance data 924 into the magnetic resonance image 926. The computer storage 334 is further shown as containing a temperature mapping module 932 which was used to reconstruct the temperature map 928 from the magnetic resonance thermometry data 927.

The computer memory is further shown as containing a high intensity focused ultrasound control module 722. The high intensity focused ultrasound control module contains computer executable code which allows the processor 628 to control the high intensity focused ultrasound system 602. The high intensity focused ultrasound control module 722 may use the magnetic resonance data 924 and/or the magnetic resonance image 926 as input to adjust the sonication of the multiple sonication points. The high intensity focused ultrasound control module 722 may use the magnetic resonance thermometry data 927 and/or the temperature map 928 as input to adjust the sonication of the multiple cavitation points 622.

In ultrasound inventions a short very high-intensity pulse or pulses may be applied to treated region prior to the volumetric thermal sonications performed with lower intensity. The purpose of the short pulses is to exploit cavitation and other bubble activity in enhancing the local absorption of acoustic energy in the focal area by exploiting nonlinear oscillations of the bubbles or by creating an acoustic barrier that prevents the wave propagation beyond the focus. The location of the pulses, and thereby the acoustic barrier or bubble cloud, may be optimized in a way that it maximizes the ablated area and/or therapy efficiency in volumetric sonications.

Passive cavitation detectors installed in predefined locations together with transducer elements capable of performing pulse-echo measurements can be used to control the formation of the acoustic barrier. The information gathered from acoustic measurements can be used in optimizing the following volumetric heating, and also in refining the feedback algorithm used to improve volumetric sonications. For example, if due to tissue heterogeneities a high-intensity cavitation pulse did not induce cavitation at certain location, a new pulse could be added to the same location, or possibly the effect could be compensated in following volumetric sonication so that into the corresponding trajectory point a longer sonication is applied.

FIG. 10 shows a pattern of cavitation and sonication locations 1000. The circles at the radiuses labeled 1002 show concentric rings of locations 1002 where cavitation is initiated. The radiuses labeled 1004 contain circles which indicate the location where sonication 1004 is performed.

FIG. 10 shows the trajectory points of a volumetric 16 mm sonications 1004 of a MR-HIFU system. One option for the corresponding cavitation pulse locations 1002 shown, i.e. there is one pulse at the center of circles and two pulse trajectories positioned between the sonication trajectories. There is no particular need for the pulse trajectories 1002 to be located between the sonication trajectories 1004; they may even be identical with the sonication trajectory points. The current choice was made purely for illustrative reasons. I some cases it may be best not to perform pulse trajectories on the outer circles since it could make the borders of the ablated region irregular. The length of the cavitation inception pulses 1002 could be 100 ms each and the amplitude should be high enough to induce inertial cavitation.

Several cavitation detectors could be used so that comparing the temporal signals would be give an understanding about the location of the bubble activity. Pulse-echo measurements detecting reflections from acoustic impedance discontinuous within beam path are very rapid (less than 0.5 ms) and could be interleaved with volumetric sonications While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS

600 medical apparatus
601 subject
602 high intensity focused ultrasound system
603 subject support
604 fluid filled chamber
606 ultrasound transducer
608 mechanism
610 mechanical actuator/power supply
612 path of ultrasound
614 ultrasound window
616 gel pad
618 sonication point
620 target volume
622 multiple cavitation locations
624 computer
626 hardware interface
628 processor
630 user interface
632 computer storage
634 computer memory
640 treatment plan
642 control module
700 medical apparatus
702 passive cavitation detector
704 acoustic sensor
710 cavitation detector data
712 cavitation spectrum
714 cavitation location
720 cavitation data calculation module
722 cavitation adjustment control module
800 therapeutic apparatus
802 diagnostic ultrasound system
804 diagnostic ultrasound transducer
806 diagnostic ultrasound data
808 diagnostic ultrasound image
810 image reconstruction module
900 medical apparatus
902 magnetic resonance imaging system
904 magnet
906 bore of magnet
908 imaging zone
910 magnetic field gradient coils
912 magnetic field gradient coils power supply
914 radio-frequency coil
916 transceiver
920 pulse sequence
922 magnetic resonance thermometry pulse sequence
924 magnetic resonance data
926 magnetic resonance image
927 magnetic resonance thermometry data
928 temperature map
930 image reconstruction module
932 temperature mapping module 934 image segmentation module
936 sonication control module
1000 cavitation and sonication location
1002 cavitation locations

The invention claimed is:

1. A medical apparatus comprising:
high intensity focused ultrasound system configured for generating focused ultrasonic energy for sonicating within a target volume of a subject, wherein the high intensity focused ultrasound system comprises an ultrasonic transducer with a controllable focus;
a memory containing machine executable instructions for controlling the medical apparatus;
a processor configured for controlling high intensity focused ultrasound system based on the instructions to:
cause ultrasonic cavitations at multiple cavitation locations on a rear surface of the target volume to form an acoustically reflective shield, wherein the multiple cavitation locations are targeted by adjusting the controllable focus; and
sonicate multiple sonication locations within the target volume in front of the acoustically reflective shield and below a threshold which induces cavitation, wherein the multiple sonication locations are targeted by adjusting the controllable focus.

2. The medical apparatus of claim 1, further including:
a passive cavitation detector, and
wherein the processor is further configured to:
measure a cavitation spectrum using the passive cavitation detector during the causing of the ultrasonic cavitation; and
control at least partially the cavitation in accordance with the cavitation spectrum by controlling the high intensity focused ultrasound system.

3. The medical apparatus of claim 1, further including:
multiple passive cavitation detectors, and
wherein the processor is further configured to:
detect a cavitation location using the multiple cavitation detectors during the causing of the ultrasonic cavitation; and
control at least partially the cavitation in accordance with the cavitation location by controlling the high intensity focused ultrasound system.

4. The medical apparatus of claim 1, further including:
an ultrasound measurement transducer configured for performing pulse-echo measurements, and
wherein the processor is further configured to:
measure at least one pulse-echo measurement with the ultrasound measurement transducer during or after the causing of the ultrasonic cavitation; and
control at least partially the cavitation in accordance with the pulse-echo measurement by controlling the high intensity focused ultrasound system.

5. The medical apparatus of claim 1, wherein the ultrasonic cavitations and the sonication of multiple sonication locations is repeated by the processor multiple times.

6. The medical apparatus of claim 1, wherein the processor is configured to arrange the multiple cavitation locations in a circular pattern.

7. The medical apparatus of claim 1 wherein the processor is configured to arrange the multiple cavitation locations to be identical with the multiple sonication locations.

8. The medical apparatus of claim 1, further including:
a magnetic resonance imaging system configured for acquiring magnetic resonance thermometry data from an imaging zone, wherein the target volume is within the imaging zone, and
wherein the processor is further configured to:
control the magnetic resonance imaging system to acquire the magnetic resonance thermometry data during the sonication of the multiple sonication locations; and
control the high intensity focused ultrasound system to adjust the sonication of the multiple sonication locations in accordance with the magnetic resonance thermometry data.

9. The medical apparatus of claim 8, wherein the magnetic resonance imaging system is further configured for acquiring phase image magnetic resonance data, and
wherein the processor is further configured to:
control the magnetic resonance imaging system to acquire the phase image magnetic resonance data during ultrasonic cavitations at multiple cavitation locations;
control the high intensity focused ultrasound system to adjust the ultrasonic cavitations in accordance with the phase image magnetic resonance data.

10. The medical apparatus of claim 1, wherein ultrasonic cavitations at the multiple cavitation locations form an acoustic barrier.

11. A method of operating a medical apparatus, wherein the medical apparatus comprises a high intensity focused ultrasound system configured for generating focused ultrasonic energy for sonicating within a target volume of a subject, wherein the high intensity focused ultrasound system comprises an ultrasonic transducer with a controllable focus, wherein the method comprises the steps of:
creating an acoustic shield by causing ultrasonic cavitations at multiple cavitation locations at a rear of the target volume using the high intensity focused ultrasound system, wherein the multiple cavitation locations are targeted by adjusting the controllable focus; and
sonicating multiple sonication locations within the target volume using the high intensity focused ultrasound system and below a threshold which induces cavitation, wherein the multiple sonication locations are targeted by adjusting the controllable focus, wherein the acoustic shield prevents acoustic propagation into tissue behind the acoustic shield during the sonicating.

12. The method of claim 11, wherein the medical apparatus further comprises a passive cavitation detector, wherein the method further comprises the steps of:
detecting a cavitation spectrum using the passive cavitation detector during the causing of the ultrasonic cavitation; and
controlling at least partially the cavitation in accordance with the cavitation spectrum by controlling the high intensity focused ultrasound system.

13. The method of claim 11, wherein the medical apparatus further comprises multiple passive cavitation detectors, wherein the method further comprises the steps of:
detecting a cavitation location using the multiple cavitation detectors during the causing of the ultrasonic cavitation; and
controlling at least partially the cavitation in accordance with the cavitation location by controlling the high intensity focused ultrasound system.

14. A non-transitory computer-readable medium carrying software which controls one or more processors to:
control a high intensity focused ultrasound system which includes at least one ultrasound transducer to form a bubble cloud by causing ultrasonic cavitations at multiple cavitation locations within the target volume; and control the high intensity focused ultrasound system to sonicate multiple sonication locations within the target volume and below a threshold which induces cavitation;

wherein the bubble cloud is configured to prevent acoustic propagation to tissue beyond the bubble cloud during the sonication.

15. A medical apparatus comprising:

a high intensity focused ultrasound system including at least one ultrasound transducer with a controllable focus;

one or more processors configured to:
- control the high intensity focused ultrasound system to cavitate tissue in a target volume to create an acoustically reflected barrier, and
- sonicate a plurality of locations adjacent the acoustically reflective barrier by applying high intensity focused ultrasound at a plurality of locations in a target region adjacent the acoustically reflective barrier, the acoustically reflective barrier and the plurality of sonication locations being configured such that the acoustically reflective barrier prevents the high intensity focused ultrasound applied during the sonication from propagating through the barrier to tissue on another side of the acoustically reflective barrier.

* * * * *